(12) United States Patent
Kangas et al.

(10) Patent No.: US 10,098,650 B2
(45) Date of Patent: Oct. 16, 2018

(54) SYSTEMS AND METHODS FOR TREATING ATHEROSCLEROTIC PLAQUE

(71) Applicant: Boston Scientific Scimed, Inc., Maple Grove, MN (US)

(72) Inventors: Steven L. Kangas, Woodbury, MN (US); Yen-Lane Chen, New Brighton, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 113 days.

(21) Appl. No.: 14/734,446

(22) Filed: Jun. 9, 2015

(65) Prior Publication Data
US 2015/0351782 A1 Dec. 10, 2015

Related U.S. Application Data

(60) Provisional application No. 62/009,570, filed on Jun. 9, 2014.

(51) Int. Cl.
*A61B 17/22* (2006.01)
*A61B 17/3207* (2006.01)

(52) U.S. Cl.
CPC .......... *A61B 17/22* (2013.01); *A61B 17/3207* (2013.01); *A61B 2017/22061* (2013.01); *A61B 2017/22065* (2013.01); *A61B 2017/22067* (2013.01); *A61B 2017/22071* (2013.01); *A61B 2017/22082* (2013.01); *A61B 2017/22084* (2013.01); *A61B 2017/22095* (2013.01); *A61B 2017/320733* (2013.01)

(58) Field of Classification Search
CPC .......... A61B 17/22; A61B 2017/22061; A61B 2017/22062; A61B 2017/22065; A61B 2017/22067; A61B 2017/22071; A61B 2017/22083; A61B 2017/22084; A61B 2017/22095; A61B 2017/3207
See application file for complete search history.

(56) References Cited

U.S. PATENT DOCUMENTS

| | | |
|---|---|---|
| 5,830,222 A | 11/1998 | Makower |
| 5,935,108 A | 8/1999 | Katoh et al. |
| 5,938,671 A | 8/1999 | Katoh et al. |
| 5,968,064 A | 10/1999 | Selmon et al. |
| 6,010,449 A | 1/2000 | Selmon et al. |

(Continued)

*Primary Examiner* — Andrew Gilbert
(74) *Attorney, Agent, or Firm* — Seager, Tufte & Wickhem LLP (57) ABSTRACT

A system and method for treating atherosclerotic plaque. The system includes a first catheter including an expandable balloon and a second catheter including a lumen in fluid communication with a distal hole. The method includes inserting the first catheter into a body lumen adjacent to a plaque formation, and deploying a balloon from the first catheter adjacent to the plaque formation. In addition, the method includes inserting the second catheter adjacent to the first catheter, and routing the distal end portion of second catheter along at least a portion of the deployed balloon of the first catheter. Further, the method includes routing at least a portion of the second catheter into a subintimal space adjacent to the atherosclerotic plaque. Furthermore, the method includes injecting a therapeutic agent into the subintimal space adjacent to the atherosclerotic plaque.

13 Claims, 6 Drawing Sheets

(56) References Cited

U.S. PATENT DOCUMENTS

| | | | |
|---|---|---|---|
| 6,068,638 A | 5/2000 | Makower | |
| 6,120,516 A | 9/2000 | Selmon et al. | |
| 6,159,225 A | 12/2000 | Makower | |
| 6,190,353 B1* | 2/2001 | Makower | A61B 1/3137 600/137 |
| 6,217,527 B1 | 4/2001 | Selmon et al. | |
| 6,217,549 B1 | 4/2001 | Selmon et al. | |
| 6,221,049 B1 | 4/2001 | Selmon et al. | |
| 6,231,546 B1 | 5/2001 | Milo et al. | |
| 6,231,587 B1 | 5/2001 | Makower | |
| 6,235,000 B1 | 5/2001 | Milo et al. | |
| 6,241,667 B1 | 6/2001 | Vetter et al. | |
| 6,398,798 B2 | 6/2002 | Selmon et al. | |
| 6,475,226 B1* | 11/2002 | Belef | A61B 1/3137 606/170 |
| 6,506,178 B1 | 1/2003 | Schubart et al. | |
| 6,508,825 B1 | 1/2003 | Selmon et al. | |
| 6,511,458 B2 | 1/2003 | Milo et al. | |
| 6,514,217 B1 | 2/2003 | Selmon et al. | |
| 6,579,302 B2 | 6/2003 | Duerig et al. | |
| 6,599,304 B1 | 7/2003 | Selmon et al. | |
| 6,638,247 B1 | 10/2003 | Selmon et al. | |
| 6,663,577 B2 | 12/2003 | Jen et al. | |
| 6,673,817 B1* | 1/2004 | Zhu | C07C 311/46 514/330 |
| 6,719,725 B2 | 4/2004 | Milo et al. | |
| 6,955,175 B2 | 10/2005 | Stevens et al. | |
| 6,997,903 B2 | 2/2006 | Wijay et al. | |
| 7,004,173 B2 | 2/2006 | Sparks et al. | |
| 7,008,411 B1* | 3/2006 | Mandrusov | A61M 25/1006 604/164.01 |
| 7,179,270 B2 | 2/2007 | Makower | |
| 7,229,421 B2 | 6/2007 | Jen et al. | |
| 7,326,238 B1 | 2/2008 | Kilpatrick et al. | |
| 7,357,794 B2 | 4/2008 | Makower et al. | |
| 7,740,623 B2 | 6/2010 | Nayak et al. | |
| 7,775,968 B2* | 8/2010 | Mathis | A61B 1/0014 600/101 |
| 7,918,859 B2 | 4/2011 | Katoh et al. | |
| 7,918,870 B2 | 4/2011 | Kugler et al. | |
| 7,938,819 B2 | 5/2011 | Kugler et al. | |
| 8,025,655 B2 | 9/2011 | Kugler et al. | |
| 8,083,727 B2 | 12/2011 | Kugler et al. | |
| 8,241,311 B2 | 8/2012 | Ward et al. | |
| 8,257,382 B2 | 9/2012 | Rottenberg et al. | |
| 8,257,383 B2 | 9/2012 | Rottenberg et al. | |
| 8,323,261 B2 | 12/2012 | Kugler et al. | |
| 8,636,712 B2 | 1/2014 | Kugler et al. | |
| 8,636,715 B2 | 1/2014 | Patel | |
| 8,721,675 B2 | 5/2014 | Rottenberg et al. | |
| 8,920,449 B2 | 12/2014 | Wilkinson | |
| 8,956,376 B2 | 2/2015 | Alvarez et al. | |
| 8,974,482 B2 | 3/2015 | Shriver | |
| 8,998,936 B2 | 4/2015 | Alvarez et al. | |
| 9,060,806 B2 | 6/2015 | Thatipelli | |
| 2001/0000041 A1 | 3/2001 | Selmon et al. | |
| 2001/0012924 A1 | 8/2001 | Milo et al. | |
| 2002/0103459 A1 | 8/2002 | Sparks et al. | |
| 2002/0128677 A1 | 9/2002 | Duerig et al. | |
| 2003/0120195 A1 | 6/2003 | Milo et al. | |
| 2003/0139763 A1 | 7/2003 | Duerig et al. | |
| 2004/0167554 A1 | 8/2004 | Simpson et al. | |
| 2004/0230219 A1 | 11/2004 | Roucher, Jr. | |
| 2005/0171478 A1 | 8/2005 | Selmon et al. | |
| 2005/0177103 A1* | 8/2005 | Hunter | A61B 17/12022 604/96.01 |
| 2006/0094930 A1 | 5/2006 | Sparks et al. | |
| 2006/0183702 A1* | 8/2006 | Diener | C12N 15/111 514/44 A |
| 2006/0184011 A1 | 8/2006 | Macaulay et al. | |
| 2006/0276749 A1 | 12/2006 | Selmon et al. | |
| 2007/0093779 A1* | 4/2007 | Kugler | A61B 17/221 604/509 |
| 2007/0093780 A1 | 4/2007 | Kugler et al. | |
| 2007/0093781 A1* | 4/2007 | Kugler | A61B 17/221 604/510 |
| 2007/0093782 A1 | 4/2007 | Kugler et al. | |
| 2007/0208368 A1 | 9/2007 | Katoh et al. | |
| 2007/0265596 A1 | 11/2007 | Jen et al. | |
| 2008/0033423 A1 | 2/2008 | Peacock, III | |
| 2008/0125748 A1 | 5/2008 | Patel | |
| 2008/0154172 A1 | 6/2008 | Mauch | |
| 2008/0200896 A1 | 8/2008 | Shmulewitz et al. | |
| 2008/0228171 A1 | 9/2008 | Kugler et al. | |
| 2008/0243065 A1 | 10/2008 | Rottenberg et al. | |
| 2008/0243067 A1 | 10/2008 | Rottenberg et al. | |
| 2008/0249397 A1 | 10/2008 | Kapadia | |
| 2009/0005755 A1 | 1/2009 | Keith et al. | |
| 2009/0088685 A1* | 4/2009 | Kugler | A61B 17/221 604/101.01 |
| 2009/0093791 A1 | 4/2009 | Heuser | |
| 2009/0124899 A1 | 5/2009 | Jacobs et al. | |
| 2009/0209910 A1 | 8/2009 | Kugler et al. | |
| 2009/0254107 A1 | 10/2009 | Katoh et al. | |
| 2009/0264826 A1 | 10/2009 | Thompson | |
| 2009/0292296 A1 | 11/2009 | Pansky et al. | |
| 2009/0299171 A1* | 12/2009 | Duffy | A61B 6/481 600/420 |
| 2009/0299402 A1 | 12/2009 | Orihashi et al. | |
| 2010/0063534 A1 | 3/2010 | Kugler et al. | |
| 2010/0069945 A1 | 3/2010 | Olson et al. | |
| 2010/0125244 A1 | 5/2010 | McAndrew | |
| 2010/0317973 A1 | 12/2010 | Nita | |
| 2011/0112564 A1 | 5/2011 | Wolf | |
| 2011/0144677 A1 | 6/2011 | Ward et al. | |
| 2011/0166591 A1 | 7/2011 | Katoh et al. | |
| 2012/0071854 A1 | 3/2012 | Kugler et al. | |
| 2012/0265233 A1* | 10/2012 | Waisman | A61M 25/1006 606/192 |
| 2012/0323269 A1 | 12/2012 | Rottenberg et al. | |
| 2013/0006167 A1 | 1/2013 | Alvarez et al. | |
| 2013/0006173 A1 | 1/2013 | Alvarez et al. | |
| 2013/0006282 A1 | 1/2013 | Wilkinson | |
| 2013/0072957 A1* | 3/2013 | Anderson | A61M 25/104 606/194 |
| 2013/0150880 A1 | 6/2013 | Anderson | |
| 2013/0245430 A1 | 9/2013 | Selmon et al. | |
| 2013/0253553 A1 | 9/2013 | Mauch et al. | |
| 2013/0317528 A1 | 11/2013 | Anderson et al. | |
| 2013/0317534 A1 | 11/2013 | Zhou et al. | |
| 2014/0018833 A1 | 1/2014 | Zhou et al. | |
| 2014/0018837 A1 | 1/2014 | Zhou et al. | |
| 2014/0180323 A1 | 6/2014 | Shriver | |
| 2014/0188149 A1 | 7/2014 | Patel | |
| 2014/0194776 A1* | 7/2014 | Gunday | A61B 17/3478 600/567 |
| 2014/0194913 A1 | 7/2014 | O'Day | |
| 2014/0200603 A1 | 7/2014 | Zhou et al. | |
| 2014/0228876 A1 | 8/2014 | Copeta et al. | |
| 2014/0243994 A1 | 8/2014 | Kapadia | |
| 2014/0275983 A1 | 9/2014 | Piccagli | |
| 2014/0277004 A1 | 9/2014 | Thatipelli | |
| 2014/0277053 A1 | 9/2014 | Wang et al. | |
| 2014/0371718 A1 | 12/2014 | Alvarez et al. | |
| 2015/0032142 A1 | 1/2015 | Silvestro | |
| 2015/0039004 A1 | 2/2015 | Sarge | |
| 2015/0051632 A1 | 2/2015 | Sina | |
| 2015/0051633 A1 | 2/2015 | Sina | |
| 2015/0112304 A1 | 4/2015 | Silvestro | |
| 2015/0112374 A1 | 4/2015 | Wilkinson | |
| 2015/0119910 A1 | 4/2015 | Alvarez et al. | |
| 2015/0165163 A1 | 6/2015 | Alvarez et al. | |
| 2015/0174371 A1 | 6/2015 | Schaeffer et al. | |

* cited by examiner

SYSTEMS AND METHODS FOR TREATING ATHEROSCLEROTIC PLAQUE

CROSS-REFERENCE TO RELATED APPLICATIONS

This application claims priority to U.S. Provisional Application Ser. No. 62/009,570, filed Jun. 9, 2014, the entirety of which is incorporated herein by reference.

TECHNICAL FIELD

The present disclosure pertains to medical devices, and methods for using medical devices. More particularly, the present disclosure pertains to medical devices for localized drug delivery for treatment of atherosclerotic plaque.

BACKGROUND

Various medical devices, such as drug-coated balloons or stents, have been developed for localized drug delivery, for example immunosuppressive and/or anti-proliferative agents to target tissue within a body for treatment. However, the amount of drug transferred to the surrounding tissue is poorly controlled and highly variable.

For example, upon inflation of a drug-coated balloon in an artery, the drug is expelled from the balloon in the form of particulates, a majority of which tend to be flushed away by blood flow prior to the balloon surface engaging a surrounding tissue within an artery. Thus, only a small percentage (1-10%) of the drug is actually absorbed by the surrounding tissue. In addition, the balloon may inadvertently mobilize during the procedure to alter the drug dosage transferred to the surrounding tissue. Further, to compensate for the drug loss, the balloon may be coated with a high dose of the drug, raising concerns about toxicity and particularization. Thus, there is a need for improved systems and methods for controlled, localized delivery of drugs.

SUMMARY

In some embodiments, a method of treating atherosclerotic plaque includes inserting a first catheter into a body lumen adjacent to a plaque formation and deploying a balloon from the first catheter adjacent to the plaque formation. The balloon has a proximal end and a distal end, where the distal end has a larger cross-section than the proximal end such that the balloon tapers from the distal end to the proximal end. Additionally, the method can include inserting a second catheter adjacent to the first catheter. The second catheter has a distal end portion, a lumen, and at least one hole. The lumen of the second catheter is in fluid communication with the hole. Further, the method includes routing the distal end portion of second catheter along at least a portion of the deployed balloon of the first catheter. Then, the method includes routing at least a portion of the second catheter into a subintimal space adjacent to the atherosclerotic plaque. The method includes removing the first catheter, injecting a therapeutic agent into the subintimal space adjacent to the atherosclerotic plaque, and removing the second catheter.

In some embodiments, a system for treating atherosclerotic plaque includes a first catheter having an expandable balloon. The expandable balloon has a proximal end and a distal end. The distal end of the balloon has a larger cross-section than the proximal end such that the expandable balloon tapers from the distal end to the proximal end when the balloon is in the expanded configuration. In addition, the system includes a second catheter having a distal end portion, a lumen, at least one hole, and a therapeutic agent. The lumen is in fluid communication with the hole, and the hole is configured to deploy the therapeutic agent. The distal end portion of the second catheter and the balloon of the first catheter are configured to direct the distal end portion of the second catheter into a subintimal space adjacent to a treatment site.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

A detailed description of the invention is hereafter described with specific reference being made to the drawings.

FIGS. 1-6 illustrate a system and method for treating atherosclerotic plaque, wherein.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

Definitions are provided for the following defined terms. It is intended that these definitions be applied, unless a different definition is given in the claims or elsewhere in this specification.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly evidences or dictates otherwise. As used in this specification and the appended claims, the term "or" is generally employed in its sense including "and/or" unless the content clearly dictates or evidences otherwise.

References in the specification to "an embodiment", "some embodiments", "other embodiments", etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure, or characteristic is described in connection with one embodiment, it should be understood that such feature, structure, or characteristic may also be used in connection with other embodiments, whether or not explicitly described unless clearly evidenced or stated to the contrary.

The following detailed description should be read with reference to the drawings in which similar elements in different drawings are numbered the same. The drawings, which are not necessarily to scale, depict illustrative embodiments and are not intended to limit the scope of the disclosure.

Some embodiments of the present disclosure are directed to a system and a method for delivering therapeutic agents to a location within a body lumen of a patient for treating atherosclerotic plaque. In some embodiments, a system for treating atherosclerotic plaque includes a first catheter, a second catheter, and a therapeutic agent. In some embodiments, the system for delivering a therapeutic agent includes a first catheter, a second catheter, a therapeutic agent, a guide wire, and a guide catheter.

In some embodiments, the method includes: 1) inserting a first catheter adjacent to a plaque formation; 2) deploying (e.g., expanding) a tapering balloon at the distal end of the first catheter; 3) inserting a second catheter adjacent to the first catheter; 4) routing the distal end portion of the second catheter along the deployed balloon; 5) piercing a subintimal tissue with the second catheter; 6) creating a hole in the subintimal layer; 7) injecting a therapeutic agent in the subintimal layer; and 8) retracting the first and second catheters out of the patient's body.

Figure 4:
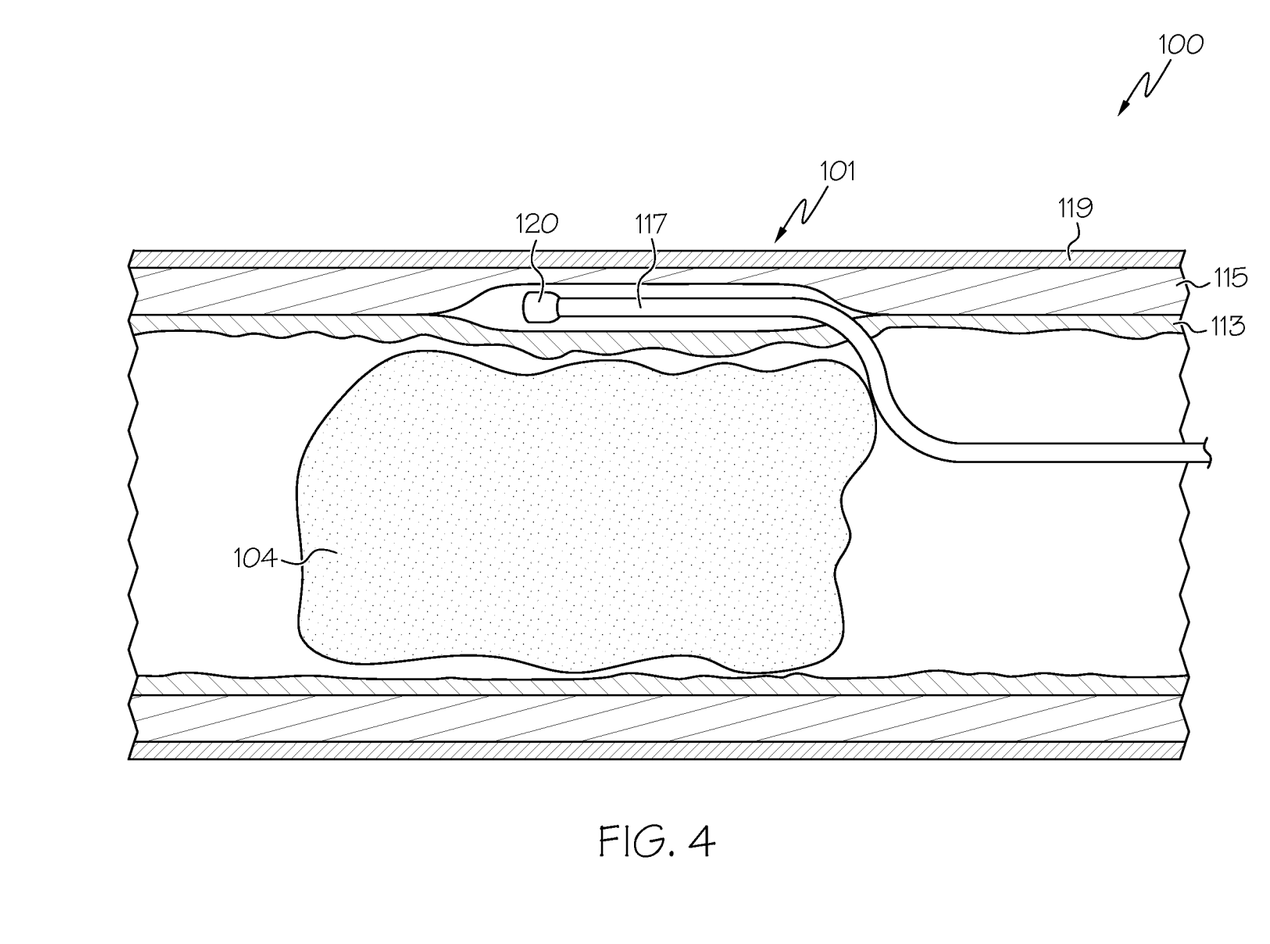
FIG. 4 illustrates the distal portion of the second catheter within the vessel wall.
Figure 5:
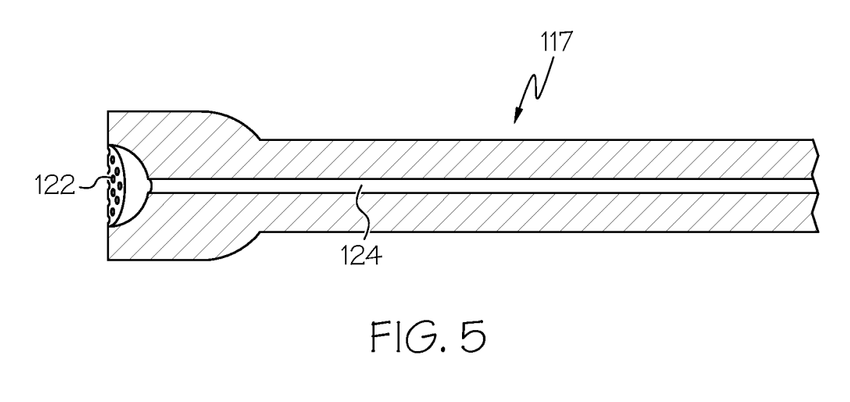
FIG. 5 is a schematic view of a distal end of the second catheter of FIG. 2.
Figure 6:
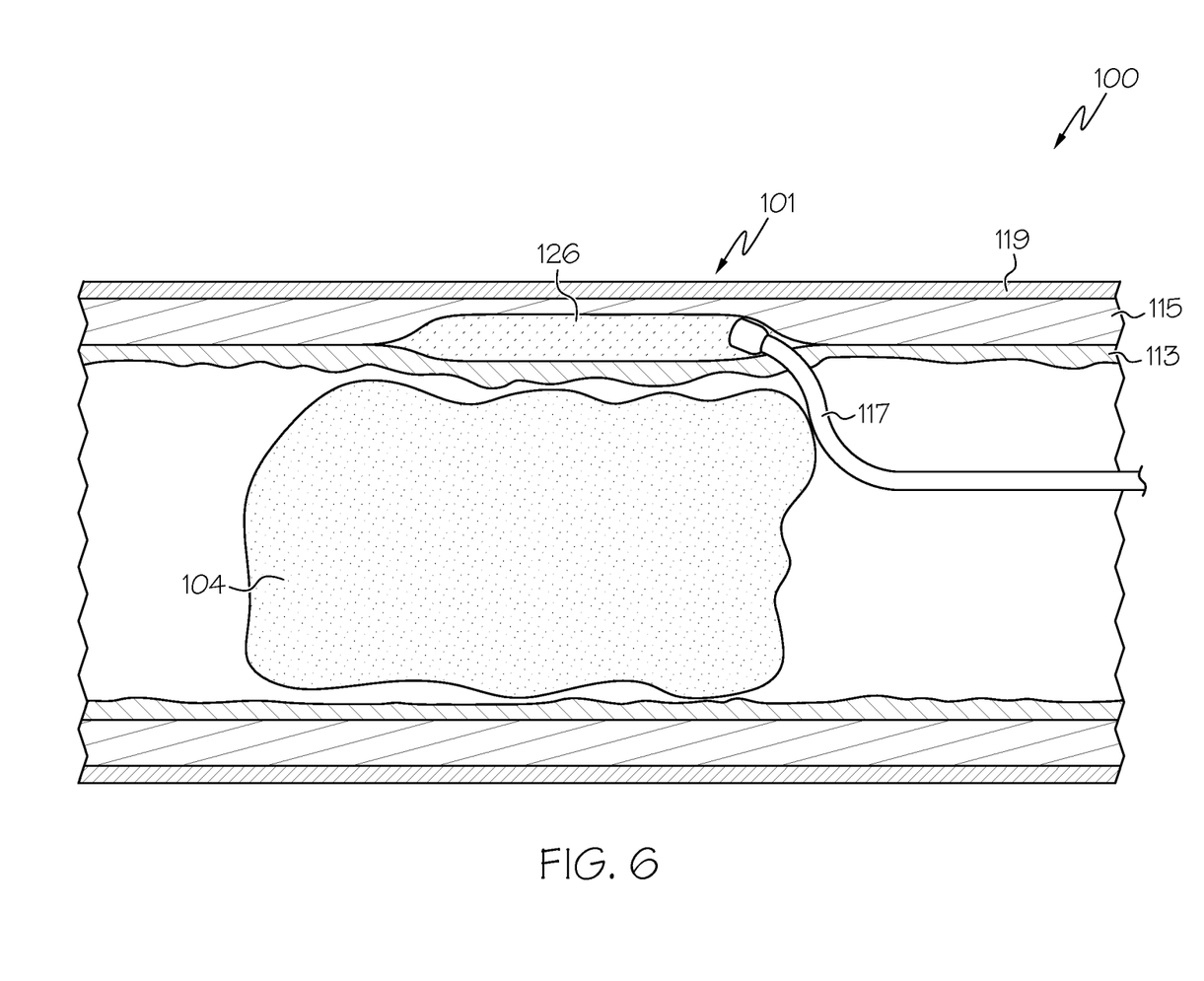
FIG. 6 depicts a therapeutic agent flowing out from the distal end of the second catheter of FIG. 5.

FIGS. 1-6 illustrate a system and method for treating atherosclerotic plaque. In some embodiments, the system includes a first catheter 102 having an expandable balloon 106 that can taper from a distal end 112 to a proximal end 114 when the balloon 106 is in the expanded configuration. In addition, in some embodiments, the system includes a second catheter 116 having a distal end portion 117, a lumen 124 (FIG. 5), one or more holes 122, and a therapeutic agent 126 (FIG. 6). The lumen 124 is in fluid communication with the one or more holes 122; the one or more holes 122 can be configured to deploy the therapeutic agent 126. In some embodiments, the distal end portion 117 of the second catheter 116 and the balloon 106 of the first catheter 102 are configured to direct the distal end portion 117 of the second catheter 116 into a subintimal space adjacent to a treatment site.

Figure 1:
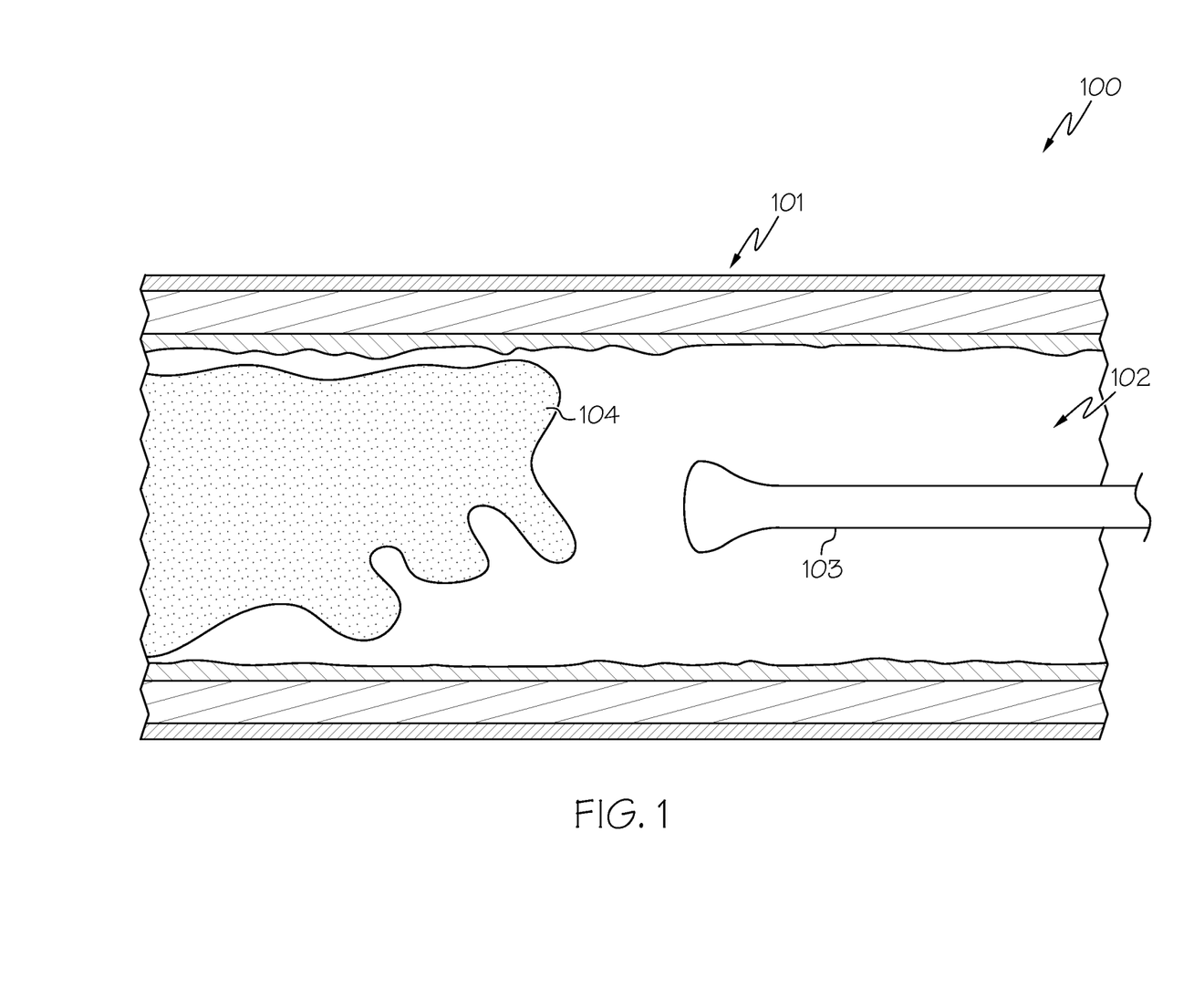
FIG. 1 depicts a distal portion of a first catheter within the blood vessel.

FIG. 1 depicts the first catheter 102 inside a blood vessel 100, having a vessel wall 101. The first catheter 102 is an elongate shaft having a distal portion 103. In some embodiments, the first catheter 102 extends proximally from the distal portion 103 to a proximal end (not shown) configured to remain outside a patient's body. The proximal end of the first catheter 102 may include a hub or handle (not shown) attached thereto for connecting other diagnostic and/or treatment devices, providing a port for facilitating interventions.

In some embodiments, the first catheter 102 has a long, thin, flexible tubular configuration. The first catheter 102 may have a cross-sectional state or configuration adapted to be received in a desired body lumen. For instance, in some embodiments, the first catheter 102 is sized and configured to accommodate passage through an intravascular path, which leads from a percutaneous access site in, for example, the femoral, brachial, or radial artery, to a targeted treatment site, for example, within a coronary artery.

The stiffness of the first catheter 102 may be modified for use in various body lumen diameters. To this end, the material used for manufacturing the first catheter 102 may include any suitable biocompatible material such as, but are not limited to, polymers, or alloys, either in combination or alone. Suitable polymeric materials include, but are not limited to: silicone, polyamide, polyether block amides, polyurethane, polyethylene, nylon, and polyethylene terephthalate. The material employed should have requisite stiffness and sufficient flexibility to maneuver through tortuous and/or stenotic lumens, avoiding any undesirable tissue injuries.

In some instances, an operator advances the distal portion of the first catheter 102 to a desired treatment site adjacent to an atherosclerotic lesion 104, within the blood vessel 100, using an outer sheath or guide catheter. For example, the first catheter 102 may be an over-the-wire catheter or a single operator exchange (SOE) catheter traversed over a guide wire (not shown) such as Stingray™ Guidewire, CholCE® Hydrophilic guide wire, or the like, to a desired treatment site adjacent to the atherosclerotic lesion 104.

Figure 2:
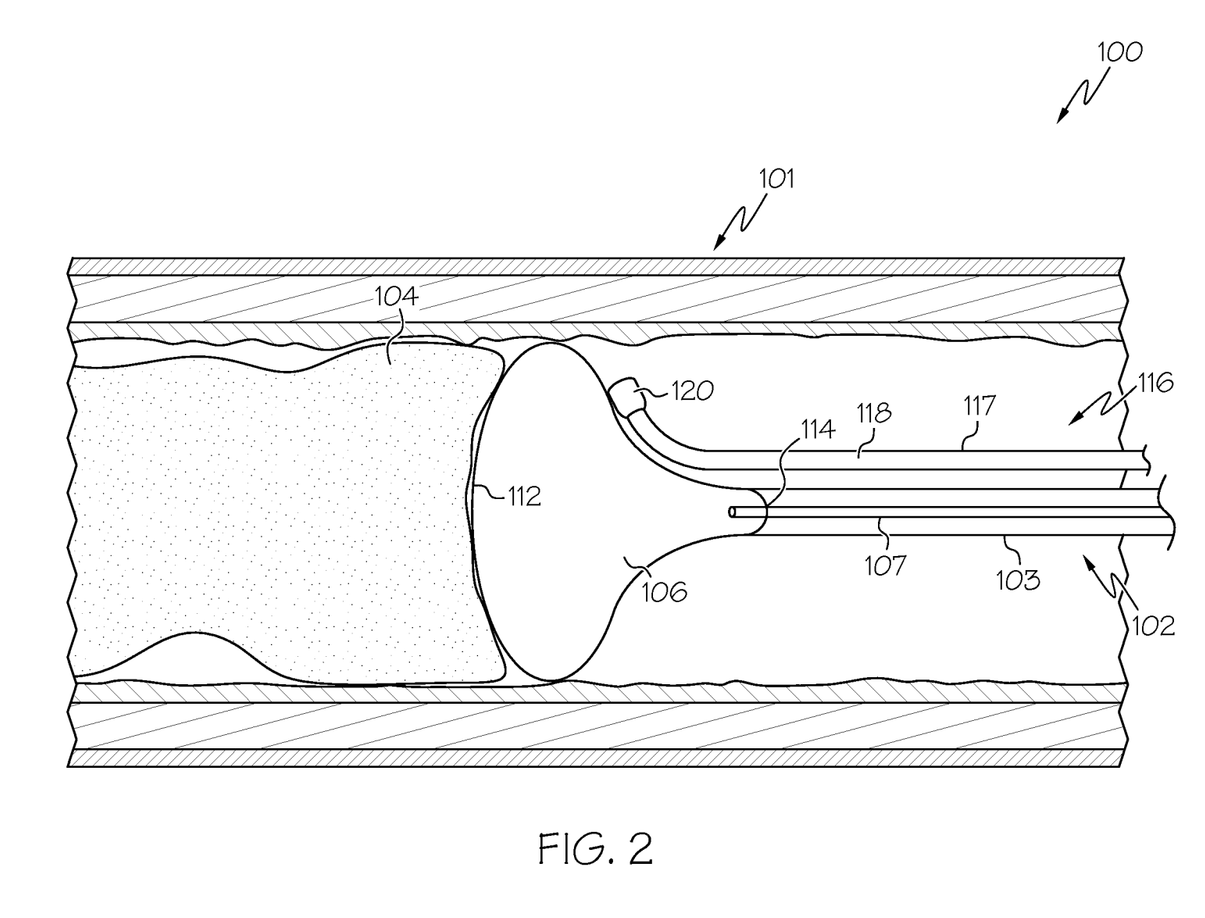
FIG. 2 illustrates a balloon at the distal portion of the first catheter along with a distal portion of a second catheter within the blood vessel.

FIG. 2 illustrates an embodiment of the first catheter 102 along with the second catheter 116 within the blood vessel 100. In some embodiments, the distal portion 103 of the first catheter 102 is a balloon catheter including the balloon 106 and an inflation lumen 107. In some embodiments, the balloon 106 is configured to inflate or deflate, upon actuation. The balloon 106 is coupled to an actuation mechanism, which may be located adjacent to or in the hub (not shown), via the inflation lumen. The actuation mechanism may include one or more components such as one or more fluid reservoirs, fluid regulators, and a control assembly. In some embodiments, the inflation lumen 107 is in fluid communication with the balloon 106 and conveys an inflation fluid, such as saline solution, for inflating the balloon 106.

In some embodiments, the balloon 106 is disposed adjacent the distal portion of the first catheter 102 and is affixed to the first catheter 102 using a biocompatible adhesive such as poly methyl methacrylate (PMMA), fibrins, or cyanoacrylate, or bonded via laser thermal welding. The balloon 106 may be coaxially positioned about the first catheter 102, having the inflation lumen 107 between an inner wall of the balloon 106 and the outer surface of the first catheter 102. The balloon 106 can further have any other suitable orientation.

Once the first catheter 102 is advanced and positioned adjacent to the atherosclerotic lesion 104, the operator may inflate the balloon 106 using the inflation fluid through the inflation lumen. Upon inflation, the balloon 106 may take on a relatively larger cross-section at the distal end 112 than the cross-section at the proximal end 114. The inflated balloon 106 can taper from the distal end 112 to the proximal end 114 of the balloon 106. For example, as shown, the inflated balloon 106 may have a conical or frusto-conical shape, though other suitable shapes may be contemplated.

After inflating the balloon 106, the operator may introduce the second catheter 116 adjacent to the first catheter 102, which may be adjacent to or at the atherosclerotic lesion 104. In some embodiments, the second catheter 116 is a cutting catheter having the distal end portion 117 and a proximal end portion (not shown). In some embodiments, the distal end portion 117 includes an elongated shaft 118 with a puncturing head 120 at a distal end of the second catheter 116. In some embodiments, the puncturing head 120 includes one or more cutting blades, a needle tip, sharp teeth, or ablation electrodes to cut through tissues and other occlusive substances present within the blood vessel in the patient's body. In some embodiments, the proximal end portion of the second catheter 116 includes a handle (not shown) to hold the second catheter 116, and an actuation mechanism, such as a pull wire (not shown) to actuate the cutting tool 120. Both the handle and the actuation mechanism may be located outside the patient's body.

In some embodiments, the puncturing head 120 has an atraumatic distal end portion 117, for example as disclosed in U.S. Pat. No. 8,512,310, to Kugler et al., issued Aug. 20, 2013; U.S. Pat. No. 8,202,246 to Kugler et al., issued Jun. 19, 2012; and U.S. Pat. No. 7,938,819, to Kugler et al., issued May 10, 2011, all of which are herein incorporated by reference.

In some embodiments, the second catheter 116 is sized and configured to accommodate passage through the intravascular path, which leads from a percutaneous access site in, for example, the femoral, brachial, or radial artery, to a targeted treatment site, for example, within a coronary artery.

The stiffness of the second catheter 116 may be adapted for use in various body lumen diameters. To this end, the material used for manufacturing the second catheter 116 may include any suitable biocompatible material such as, but are not limited to, polymers, or alloys, either in combination or alone. Suitable polymeric materials may include, but are not limited to, silicone, polyamide, polyether block amides, polyurethane, polyethylene, nylon, and polyethylene terephthalate. The material employed may have enough stiffness for use in various body lumen diameters, and sufficient flexibility to maneuver through tortuous and/or stenotic lumens, avoiding any undesirable tissue injuries. A variety of catheters known in the art, for example, CrossBoss™ Coronary CTO Crossing Catheter, may be used as the second catheter 116.

In some embodiments, the distal end portion 117 is routed along an outer surface of the first catheter 102. As shown, the puncturing head 120 slides along the tapered surface of the balloon 106 towards the wall of the blood vessel 100.

Figure 3:
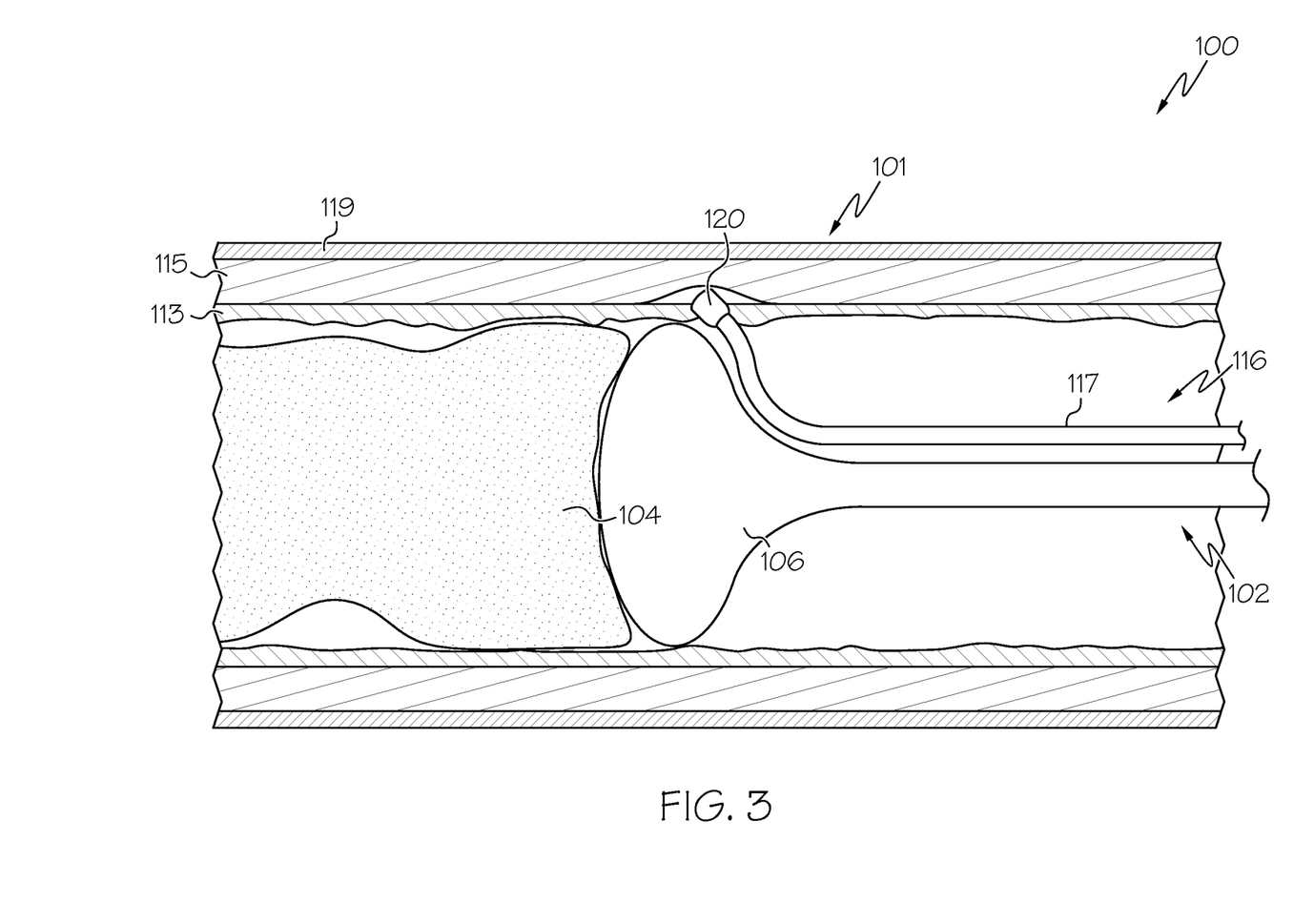
FIG. 3 depicts the balloon and the second catheter of FIG. 2 in communication with a vessel wall within the blood vessel.

FIG. 3 depicts the second catheter 116 just prior to its entering the subintimal space of the vessel wall 101. The vessel wall 101 is typically made of three layers of tissue: tunica intima 113, tunica media 115, and tunica adventitia 119. Tunica intima 113 is the innermost tissue layer of a blood vessel, and is made of one layer of endothelial cells. The endothelial cells are in direct contact with the blood flow. Tunica media 115 is the middle tissue layer of a blood vessel, and is made up of smooth muscle cells and elastic tissue. Tunica adventitia 119 is the outermost layer of tissue surrounding a blood vessel. Tunica adventitia 119 is mostly composed of collagen, which serves to anchor the blood vessels to organs.

FIG. 4 illustrates the distal end portion 117 within the vessel wall 101. As shown, in some embodiments, the operator may route the distal end portion 117 into the subintimal space adjacent to the atherosclerotic lesion 104. As used herein, the subintimal space refers to the region between tunica intima 113 and tunica media 115 layers of the vessel wall 101. Penetration of the subintimal space by the distal end portion 117 forces the tunica intima 113 and tunica media 115 layers to part from each other, in the regions proximate to the distal end portion 117, and creates a pocket in the vessel wall 101 adjacent to the atherosclerotic lesion 104. At this juncture, in some embodiments, the balloon 106 may be deflated and the first catheter 102 may be retracted from the patient's body.

In some embodiments, the second catheter 116 comprises one or more balloons, which can be used to increase the size of the pocket formed in the subintimal space or orient the second catheter 116 within the subintimal space, as shown for example in U.S. Pat. No. 8,202,246 to Kugler et al., issued Jun. 19, 2012.

FIG. 5 is a schematic of an embodiment of the distal end portion 117 of the second catheter 116. The second catheter 116 may include one or more hole(s), such as the hole 122, at its distal tip. In some embodiments, the lumen 124 is in fluid communication with the hole 122. In some embodiments, the lumen 124 extends through the second catheter 116 from the hole 122 to a port on the proximal end portion (not shown). In this way, the operator can inject the therapeutic agent 126 (shown in FIG. 6) via the port on the proximal end portion and the therapeutic agent 126 flows through the lumen 124 and is injected into the subintimal space thorough the hole 122.

FIG. 6 depicts the therapeutic agent 126 flowing out of the distal end portion 117 of the second catheter 116 and into the subintimal space. In some embodiments, the operator retracts the distal end portion 117 out of the subintimal space after filling the pocket created in the subintimal space. The subintimal space may hold the therapeutic agent 126 as a reservoir for controlled release into the atherosclerotic lesion 104 over a period, ranging from a few hours to a few months. In some embodiments, after retracting the distal end portion 117 out of the subintimal space, the operator retracts the second catheter 116 out of the patient's body. The second catheter 116 can be retracted prior to retraction of the first catheter 102 or after retraction of the first catheter 102.

In some embodiments, the therapeutic agent 126 includes a combination of an excipient and one or more drugs. Also, in some embodiments, the therapeutic agent 126 includes drugs for treatment of atherosclerotic plaque, such as the atherosclerotic lesion 104. For example, the therapeutic agent 126 may include one or more chelating agents for calcium complexation of plaque, emulsifying agents for dissolving lipid-rich plaque, or anti-inflammation agents to inhibit the development of atherosclerosis, or drugs to reverse plaque formation. In some embodiments, the therapeutic agent 126 includes recombinant high density lipoprotein (rHDL), chelation agents, corticosteroids, progesterone, dexamethasone, paclitaxel, sirolimus, everolimus, or any other drug suitable for treatment of atherosclerosis. The drugs may be in the form of micro particles or nano particles dispersed in a liquid or hydrogel-based medium (excipient). The micro particles or nano particles may be pure agents or compounded with a biodegradable polymer such as poly (lactic-co-glycolic) acid (PLGA) (excipient).

As discussed, in some embodiments, the therapeutic agent 126 includes a hydrogel which provides an excipient medium to transfer the drug to the target tissue, such as the atherosclerotic lesion 104. The hydrogel-based excipient medium may help in storing the drug in the subintimal space and favorably change its pharmacokinetic behavior. Some examples of the therapeutic agent 126 include polysaccharides, such as a mixture of alginates, a drug such as those mentioned above, and calcium salt that cross link the hydrogel-based excipient medium to prevent washout of the drug. Other suitable hydrogels include gelatin, hyaluronic acid, polyvinylpyrrolidone (PVP), cellulosics, collagen, which may be used as an excipient medium. The therapeutic agent 126 may be a pure dispersion of the drug in the hydrogel or drug encapsulated in a microsphere such as poly(lactic-co-glycolic) acid (PLGA). Alternatively, PLGA micro- or nano-spheres can be dispersed in water or saline.

In some embodiments, the second catheter 116 may include an electrode (not shown) on the distal end portion 117. After retraction of the distal end portion 117 out of the subintimal space, the operator may use the electrode to cauterize the opening (not shown) of the pocket created in the intimal layer 113 tissue of the vessel wall 101 by the penetration of the distal end portion 117, in order to close the incision opening of the pocket in the vessel wall. Cauterization of the subintimal tissue at the opening of the pocket may prevent the therapeutic agent from leaving the subintimal space through the pocket opening (instead of diffusion through the vessel wall) to reduce loss of drug to the blood stream.

In some embodiments, the therapeutic agent 126 contained in the subintimal space provides a highly localized drug-delivery to the atherosclerotic lesion 104. Additionally, the contained therapeutic agent 126 may prevent or reduces systemic loss of the drug into the blood flow. And, microspheres containing drug particulates in the therapeutic agent 126 can serve as a depot that releases active ingredient onto the atherosclerotic lesion 104 over time to treat atherosclerotic arterial vessels. The drug particles may release at a controlled rate from the therapeutic agent within the capillaries of the tunica intima 113 layer and interact with the plaque for treatment. Time release of the drug may increase its efficacy without overloading and may provide long-term treatment of the atherosclerotic lesion 104.

Although the system and methods disclosed herein relate to treatment of atherosclerotic plaque, a person of ordinary skill in the art may contemplate other treatment procedures where the disclosed system and methods may be used. For example, the systems and methods disclosed herein may be used to deliver drugs to a tumor, such as cancerous tissue in the liver of a patient.

A description of some embodiments of the atherosclerotic plaque treatment system and method are contained in one or more of the following numbered statements:

Statement 1. A system for treating atherosclerotic plaque comprising:
a first catheter having an expandable balloon, the expandable balloon having a proximal end and a distal end, the distal end having a larger cross-section than the proximal end;
a second catheter having a distal end portion, a lumen, at least one hole, and a therapeutic agent, the lumen being in fluid communication with the at least one hole, the hole being configured to deploy the therapeutic agent;
wherein the distal end portion of the second catheter and the balloon of the first catheter are configured to direct the distal end portion of the second catheter into a subintimal space adjacent to a treatments site.

Statement 2. The system of statement 1, wherein the expandable balloon tapers from the distal end to the proximal end thereof when the balloon is in the expanded configuration.

Statement 3. The system of any one of the preceding statements, wherein the first catheter has an inflation lumen in fluid communication with the expandable balloon.

Statement 4. The system of any one of the preceding statements, wherein the first catheter is formed from silicone, polyamide, polyether block amide, polyurethane, polyethylene, nylon, or polyethylene terephthalate.

Statement 5. The system of any one of the preceding statements, wherein the expandable balloon is conical or frusto-conical in shape.

Statement 6. The system of any one of the preceding statements, wherein the second catheter is configured to inject the therapeutic agent into the subintimal space.

Statement 7. The system of any one of the preceding statements, wherein the distal end portion of the second catheter comprises a puncturing head.

Statement 8. The system of statement 7, wherein the puncturing head comprises at least one cutting blade.

Statement 9. The system of statement 7, wherein the puncturing head comprises an ablation electrode.

Statement 10. The system of claim any one of the preceding statements, wherein the at least one hole comprises a plurality of holes.

Statement 11. The system of any one of the preceding statements, wherein the therapeutic agent comprises an excipient agent and a drug.

Statement 12. The system of statement 11, wherein the excipient is a hydrogel.

Statement 13. The system of statement 12, wherein the hydrogel is gelatin, hyaluronic acid, polyvinylpyrrolidone, collagen, or a cellulosic.

Statement 14. The system of any one of the preceding statements, wherein the therapeutic agent comprises a plurality of drugs.

Statement 15. The system of any one of the preceding statements, wherein the therapeutic agent comprises a time release drug.

Statement 16. The system of any one of the preceding statements, wherein the therapeutic agent includes poly (lactic-co-glycolic) acid.

Statement 17. A method of treating atherosclerotic plaque comprising:
inserting a first catheter into a body lumen adjacent to a plaque formation;
deploying a balloon from the first catheter adjacent to the plaque formation, wherein the balloon has a proximal end and a distal end, the distal end having a larger cross-section than the proximal;
inserting a second catheter adjacent to the first catheter, the second catheter having a distal end portion, a lumen, and at least one hole, the lumen being in fluid communication with the at least one hole;
routing the distal end portion of second catheter along at least a portion of the deployed balloon of the first catheter;
routing at least a portion of the second catheter into a subintimal space adjacent to the atherosclerotic plaque;
removing the first catheter;
injecting a therapeutic agent into the subintimal space adjacent to the atherosclerotic plaque; and
removing the second catheter.

Statement 18. The method of statement 17 further comprising the step of inserting a guidewire.

Statement 19. The method of statement 17, wherein the step of injecting a therapeutic agent into the subintimal space comprises flowing the therapeutic agent through the lumen and out of the at least one hole.

Statement 20. The method of statement 17, wherein the balloon tapers from the distal end to the proximal end thereof.

Statement 21. The method of statement 17, wherein the step of injecting a therapeutic agent into the subintimal space comprises deploying a therapeutic agent from the at least one hole.

Statement 22. The method of statement 17, wherein the therapeutic agent includes a biodegradable polymer.

Statement 23. The method of statement 17, wherein the therapeutic agent includes a drug selected from the group consisting of: recombinant HDL, chelation agents, corticosteroids, progesterone, or dexamethasone.

Statement 24. The method of statement 17, wherein the therapeutic agent is in the form of microparticle or nanoparticle.

Statement 25. The method of statement 17, wherein the therapeutic agent includes an excipient and a drug.

Statement 26. The method of statement 17, wherein the therapeutic agent includes an alginate, a drug, and a calcium salt.

Statement 27. The method of statement 17, wherein the therapeutic agent includes poly(lactic-co-glycolic) acid.

Statement 28. The method of statement 17, wherein the therapeutic agent includes a hydrogel.

Statement 29. The method of statement 28, wherein the hydrogel is gelatin, hyaluronic acid, polyvinylpyrrolidone, collagen, or a cellulosic.

Statement 30. A system for treating atherosclerotic plaque comprising:

a first catheter having an expandable balloon, the expandable balloon having a proximal end and a distal end, the distal end having a larger cross-section than the proximal end such that the expandable balloon tapers from the distal end to the proximal end when the balloon is in the expanded configuration;

a second catheter having a distal end portion, a lumen, at least one hole, and a therapeutic agent, the lumen being in fluid communication with the at least one hole, the hole being configured to deploy the therapeutic agent;

wherein the distal end portion of the second catheter and the balloon of the first catheter are configured to direct the distal end portion of the second catheter into a subintimal space adjacent to a treatments site.

Statement 31. The system of statement 30, wherein the first catheter has an inflation lumen in fluid communication with the expandable balloon.

Statement 32. The system of statement 30, wherein the first catheter is formed from silicone, polyamide, polyether block amide, polyurethane, polyethylene, nylon, or polyethylene terephthalate.

Statement 33. The system of statement 30, wherein the expandable balloon is conical or frusto-conical in shape.

Statement 34. The system of statement 30, wherein the second catheter is configured to inject the therapeutic agent into the subintimal space.

Statement 35. The system of statement 30, wherein the distal end portion of the second catheter comprises a puncturing head.

Statement 36. The system of statement 35, wherein the puncturing head comprises at least one cutting blade.

Statement 37. The system of statement 30, wherein the at least one hole comprises a plurality of holes.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method of treating atherosclerotic plaque comprising:
    inserting a first catheter into a body lumen adjacent to a plaque formation;
    inflating a balloon from the first catheter adjacent to the plaque formation, wherein the balloon has a proximal end and a distal end;
    inserting a second catheter adjacent to the first catheter, the second catheter having a distal end portion, a lumen, and at least one hole, the lumen being in fluid communication with the at least one hole;
    advancing the distal end portion of the second catheter distally along and in contact with an exterior surface of a balloon wall of the inflated balloon of the first catheter after the first catheter has been positioned adjacent to the plaque formation;
    advancing at least a portion of the second catheter distally into a subintimal space adjacent to the atherosclerotic plaque;
    removing the first catheter while maintaining the second catheter in the subintimal space;
    injecting a therapeutic agent into the subintimal space adjacent to the atherosclerotic plaque; and
    removing the second catheter;
    wherein the balloon wall includes an interior surface in fluid communication with an inflation lumen of the first catheter, and the exterior surface of the balloon wall is in fluid communication with fluid within the body lumen.

2. The method of claim 1, wherein the step of injecting a therapeutic agent into the subintimal space comprises flowing the therapeutic agent through the lumen and out of the at least one hole.

3. The method of claim 1, wherein the balloon tapers from the distal end to the proximal end thereof.

4. The method of claim 1, wherein the step of injecting a therapeutic agent into the subintimal space comprises deploying a therapeutic agent from the at least one hole.

5. The method of claim 1, wherein the therapeutic agent includes a biodegradable polymer.

6. The method of claim 1, wherein the therapeutic agent includes a drug selected from the group consisting of: recombinant HDL, chelation agents, corticosteroids, progesterone, or dexamethasone.

7. The method of claim 1, wherein the therapeutic agent is in the form of microparticle or nanoparticle.

8. The method of claim 1, wherein the therapeutic agent includes an excipient and a drug.

9. The method of claim 1, wherein the therapeutic agent includes an alginate, a drug, and a calcium salt.

10. The method of claim 1, wherein the therapeutic agent includes a hydrogel.

11. The method of claim 10, wherein the hydrogel is gelatin, hyaluronic acid, polyvinylpyrrolidone, collagen, or a cellulosic.

12. A method of treating atherosclerotic plaque comprising:
    inserting a catheter having a balloon on a distal end region thereof into a lumen of a blood vessel until the balloon is positioned adjacent to a plaque formation;
    inflating the balloon adjacent to the plaque formation until the balloon contacts an inner layer of a wall of the blood vessel at a contact location;
    thereafter, distally advancing a medical device along an exterior of the catheter and along and in contact with an exterior surface of a balloon wall of the inflated balloon and into a subintimal space in the wall of the blood vessel,
    wherein the medical device enters into the subintimal space at a location proximal of the contact location between the balloon and the inner layer of the wall of the blood vessel;
    wherein the balloon wall includes an interior surface in fluid communication with an inflation lumen of the catheter, and the exterior surface of the balloon wall is in fluid communication with fluid within the blood vessel.

13. The method of claim 12, further comprising:

removing the catheter while maintaining the medical device in the subintimal space; and thereafter, removing the medical device.

\* \* \* \* \*